(12) United States Patent
Castillo-Welter et al.

(10) Patent No.: US 8,974,584 B2
(45) Date of Patent: Mar. 10, 2015

(54) GAS SCRUBBER HAVING AN INTEGRATED HEAT EXCHANGER

(75) Inventors: Frank Castillo-Welter, Friedrichsdorf (DE); Christoph Steden, Oberursel (DE); Dominic Walter, Darmstadt (DE); Georg Ehring, Frankfurt (DE); Martin Müller-Hasky, Heusenstamm (DE)

(73) Assignee: Lurgi GmbH, Frankfurt am Main (DE)

( * ) Notice: Subject to any disclaimer, the term of this patent is extended or adjusted under 35 U.S.C. 154(b) by 305 days.

(21) Appl. No.: 13/508,937

(22) PCT Filed: Sep. 24, 2010

(86) PCT No.: PCT/DE2010/001136
§ 371 (c)(1),
(2), (4) Date: Jun. 5, 2012

(87) PCT Pub. No.: WO2011/057597
PCT Pub. Date: May 19, 2011

(65) Prior Publication Data
US 2012/0234167 A1   Sep. 20, 2012

(30) Foreign Application Priority Data

Nov. 11, 2009   (DE) .......................... 10 2009 052 506

(51) Int. Cl.
*B01D 47/00* (2006.01)
*B01D 53/18* (2006.01)
*B01D 53/78* (2006.01)
*C07D 251/60* (2006.01)
*F28D 9/00* (2006.01)
*F28F 3/14* (2006.01)
(Continued)

(52) U.S. Cl.
CPC ................ *B01D 53/18* (2013.01); *B01D 53/78* (2013.01); *C07D 251/60* (2013.01); *F28D 9/0006* (2013.01); *F28F 3/14* (2013.01); *F28F 13/06* (2013.01); *B01D 53/77* (2013.01); *B01D 2251/2067* (2013.01); *B01D 2257/70* (2013.01)
USPC ................ 96/242; 96/234; 96/271; 261/156; 261/157

(58) Field of Classification Search
None
See application file for complete search history.

(56) References Cited

U.S. PATENT DOCUMENTS

| 3,682,911 | A | * | 8/1972 | Kaasenbrood et al. | ........ 544/201 |
| 4,138,560 | A | * | 2/1979 | Hillenbrand et al. | ......... 544/203 |
| 5,507,356 | A | * | 4/1996 | Roth et al. | .................... 165/111 |

(Continued)

FOREIGN PATENT DOCUMENTS

| DE | 4300131 A1 | 7/1994 |
| EP | 0862036 A2 | 9/1998 |

(Continued)

OTHER PUBLICATIONS

International Search Report for PCT/DE2010/001136 dated Feb. 14, 2011.

(Continued)

*Primary Examiner* — Duane Smith
*Assistant Examiner* — Phillip Shao
(74) *Attorney, Agent, or Firm* — Norris McLaughlin & Marcus P.A.

(57) ABSTRACT

A gas scrubber, equipped with heat exchanger surfaces constructed of thermoplates, suitable for cooling and cleaning a hot gas by avoiding an excessive thermal load of the washing liquid.

7 Claims, 3 Drawing Sheets

(51) Int. Cl.
*F28F 13/06* (2006.01)
*B01D 53/77* (2006.01)

(56) References Cited

U.S. PATENT DOCUMENTS

| | | |
|---|---|---|
| 5,603,377 A | 2/1997 | Fujii et al. |
| 6,192,704 B1 * | 2/2001 | Hiro et al. ................. 62/484 |
| 6,883,788 B1 * | 4/2005 | Tagamolila et al. .......... 261/128 |
| 7,410,622 B2 * | 8/2008 | Olbert et al. ................. 422/198 |
| 7,772,410 B2 * | 8/2010 | Hechler et al. ............... 549/248 |
| 2005/0020851 A1 | 1/2005 | Olbert et al. |
| 2009/0321057 A1 * | 12/2009 | Daly ........................... 165/111 |

FOREIGN PATENT DOCUMENTS

| | | |
|---|---|---|
| EP | 1138676 A1 | 10/2001 |
| GB | 1147908 A | 4/1969 |
| WO | 96/07467 A1 | 3/1996 |

OTHER PUBLICATIONS

English language translation of DE4300131 found on esp@cenet.com.

* cited by examiner

GAS SCRUBBER HAVING AN INTEGRATED HEAT EXCHANGER

This application is a 371 application of PCT/ DE2010/ 001136 filed Sep. 24, 2010, which claims priority to the German application DE 10 2009 052 506.8 filed Nov. 11, 2009.

This invention relates to a gas scrubber, with one or more heat exchangers integrated in the apparatus housing, for cooling the gas/liquid mixture formed of the gas to be cleaned and the washing liquid.

The invention also relates to a method for using such gas scrubber.

Scrubbers and methods for cooling and cleaning are known.

In particular applications for gas scrubbers, in which the temperature of the gas to be cooled lies far above that of the washing liquid and at the same time heating of the washing liquid should be prevented as far as possible, in order to avoid its evaporation or chemical decomposition, it is required to integrate heat exchangers directly in the scrubber housing, in the flow of the gas/liquid mixture.

In the German laid-open specification 25 25 781 a corresponding case for the treatment of process waste gas from a melamine synthesis is described. There is used a gas scrubber with an integrated cooler, in order to prevent that the urea used as washing liquid is heated too much by the process waste gas flowing into the scrubber with high temperature and decomposition products of the urea formed thereby contaminate the heat exchanger surface.

From Ullmann's Encyclopedia of Industrial Chemistry, Sixth Edition, 1998 Electronic Release, it can be taken that for the same application a substantially cylindrical upright gas scrubber with integrated heat exchanger is used, which is traversed by the gas and by the washing liquid from top to bottom, in cocurrent flow.

Both publications are silent on the construction of the heat exchanger(s) integrated in the scrubber.

It is, however, known to the skilled person that for the applications described in the aforementioned documents tube bundle heat exchangers are used, namely both of the type where the gas/liquid mixture to be cooled is guided around the tubes and of the type where it is guided through the tubes.

When the gas/liquid mixture is guided around the tubes, the tubes are installed vertically, and hence transverse to the flow direction, in the gas scrubber. It is possible to install the tubes transversely through the scrubber, from wall to wall, or to vertically introduce U-shaped tube bundle heat exchangers through the column wall into the scrubber. The construction of guiding the tubes from wall to wall has the disadvantage that the heat exchanger is accessible for cleaning and repair work only with great difficulty; moreover this construction is very costly. The scrubber construction in which U-shaped tube bundle heat exchangers are laterally pushed into the scrubber cross-section is less expensive and more maintenance-friendly. However, it has the disadvantage that the heat exchanger surface is distributed over the scrubber cross-section only non-uniformly, so that the gas/liquid mixture is cooled only non-uniformly. In the construction in which the gas/liquid mixture is guided through the heat exchanger tubes, the tubes extend parallel to the vertical axis of the scrubber and the tube plates fill up the entire cross-section of the scrubber. The disadvantage of this construction consists in the tendency of the tubes to clogging and hence in a high cleaning effort.

Therefore, it has been the object to design an improved gas scrubber also suitable for cooling the process media, with which a more uniform cooling is possible and which can be operated with little cleaning and maintenance effort.

In the present invention, this object is solved by using heat exchangers constructed of thermoplates in the gas scrubber.

Further developments, advantages and possible applications of the invention can also be taken from the following description and the drawing. All features described and/or illustrated form the subject-matter of the invention per se or in any combination, independent of their inclusion in the claims or their back-reference.

Thermoplates and heat exchangers constructed of the same have been known since the 1970ies (U.S. Pat. No. 3,822,742; W. Mählthaler, Fachhochschule Mannheim, AA No. 13). Thermoplates are formed of two plates of equal thickness, which are placed onto each other and welded to each other along the edge by a circumferential seam. On the surface, the plates are connected by regularly arranged spot welds. By generating a hydaulic or pneumatic pressure between the plates, the same are formed to be obtain the characteristic quilted shape of the thermoplates. The space thus obtained between the plates serves to receive the heat transfer or cooling medium. Since no flow paths are defined in this space, thermoplates are particularly useful for evaporation cooling, since the steam bubbles obtained can rise and leave the thermoplate unimpededly.

In accordance with the invention, numerous thermoplates are combined to a heat exchanger and, according to a preferred embodiment of the invention, are integrated in the cylindrical gas scrubber in a vertical upright position, parallel to the vertical axis, wherein the entire cross-section of the gas scrubber is filled up and there is a free distance from plate to plate of 7 to 45 mm, preferably of 15 to 30 mm.

By using this type of heat exchanger, a specific density of heat exchanger surface arranged uniformly over the cross-section of the gas scrubber is available.

For cost reasons, it is also possible to incorporate such heat exchangers with square or rectangular cross-section into the circular cross-section of the scrubber. The circular segments around the heat exchanger spared thereby must then be covered by means of corresponding baffle plates, in order to avoid uncooled edge flows.

An advantage of heat exchangers constructed of thermoplates consists in that in relation to the heat exchanger surface provided by them they only cause a small pressure loss during the passage of the gas/liquid mixture. An important advantage of this construction is the self-cleaning capability of the heat exchanger with this procedure, as in case particle lumps originating from the melamine synthesis get stuck between the thermoplates, enough room is left for the gas/liquid flow to surround and carry away such lump. When flowing through heat exchanger tubes, however, such lump would lead to the clogging of the tube, without a possibility for self-cleaning.

Therefore, a preferred aspect of the invention consists in that the washing liquid and the process gas together flow through the gaps between the thermoplates and the cooling medium flows within the thermoplates.

A further preferred aspect of the invention is characterized in that downstream before the heat exchanger flow baffles are mounted, each consisting of a rectangular sheet-metal plate, which are arranged parallel to each other, wherein the plates are arranged such that their lower, long edges extend parallel to the upper edges of the thermoplates at a distance of 5 to 15 cm, wherein the lower edges of the baffle plates have the same distance to each other as the thermoplates, wherein the short edges of the baffle plates have an equal length of 10 to 30 cm, and wherein the baffle plates are arranged at an angle of less than 90° relative to the vertical axis of the gas scrubber. The task of these baffle plates consists in directing the flow of the gas/liquid mixture against the thermoplates, in order to further improve the heat exchange.

A further preferred aspect of the invention is characterized in that the flow baffles are arranged in rows lying one beside the other and extending parallel to each other, with alternating angles F.

To increase the turbulence of the flow of the gas/liquid mixture to be cooled and hence the heat transfer, the thermoplates of successive heat exchangers are arranged offset with respect to each other by an angle of 90° in accordance with a further aspect of the invention. The construction of a gas scrubber according to the invention in particular is suitable for cooling and cleaning the process waste gas from a melamine synthesis, which is carried out in the gas phase and at pressures of not more than 10 bar. This is characteristic for the so-called BASF process, as it is described in Ullmann's Encyclopedia of Industrial Chemistry, Sixth Edition, 1998 Electronic Release.

A further preferred aspect of the invention is characterized in that the cooling medium present within the thermoplates is evaporated by absorbing the heat from the gas/liquid mixture. In this way, the temperature of the heat exchanger surface can exactly and uniformly be adjusted.

With reference to Example 1, with the material stream table 1 and the drawing, consisting of FIGS. 1 to 3, the method will now be explained.

Example 1

Figure 1:
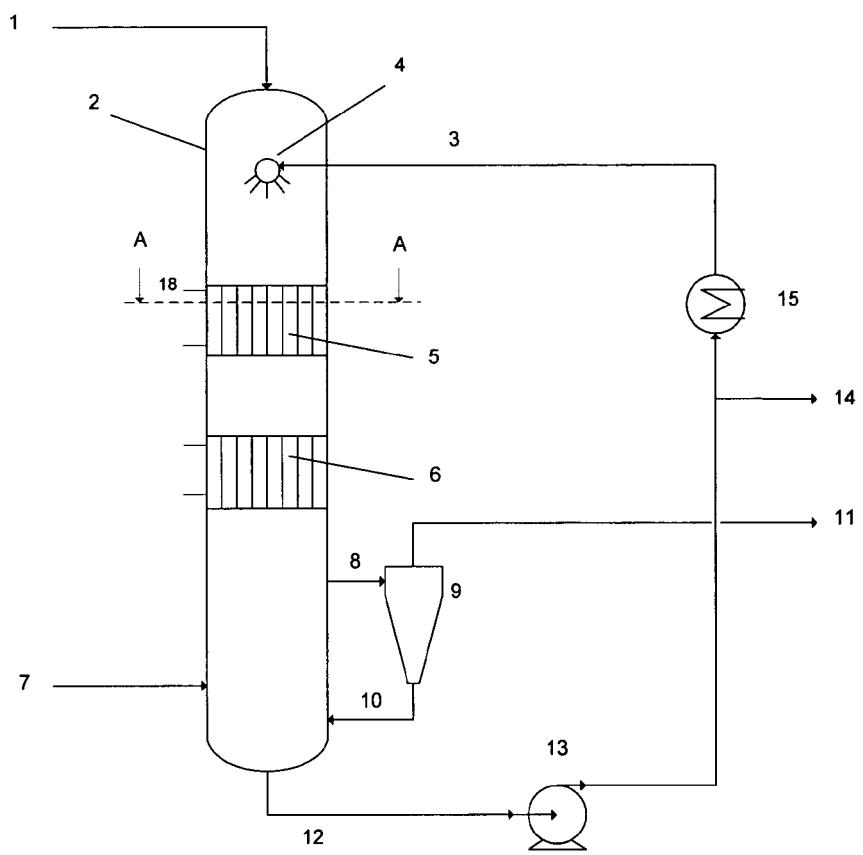
FIG. 1 is a plant for washing waste gas from a melamine synthesis process.

FIG. 1 shows a plant for washing a process waste gas of a melamine synthesis, which chiefly consists of ammonia and carbon dioxide as well as urea and isocyanic acid residues, comprising the gas scrubber (2), the separator (9), the circulating pump (12) and the cooler (13). Coming from the non-illustrated melamine synthesis, the process waste gas stream (1) enters at the head of the cylindrical gas scrubber (2). As material stream (3), the urea-containing melt used as washing liquid is introduced into the gas scrubber. By means of a nozzle system (4), the washing liquid (3) is distributed in the process waste gas (1), so that a gas/liquid mixture is formed. Subsequently, the gas/liquid mixture flows through the heat exchangers (5) and (6). In accordance with the invention, the heat exchangers are constructed of thermoplates. For cooling the gas/liquid mixture, boiling water with a temperature of 125° C. is present in the thermoplates. The steam generated by the absorbed heat leaves the thermoplates via the collecting conduit (18), is condensed (not shown), whereupon the condensate is again supplied to the heat exchanger. After flowing through the heat exchangers (5) and (6), the process waste gas and the washing liquid are separated from each other. For this purpose, the gas/liquid mixture is passed via conduit (8) from the scrubber into gas gas/liquid separator (9). Via conduit (11), the gas leaves the separator (9) and can be used as process gas in the melamine synthesis. Via conduit (10), the urea-containing melt is recirculated from the gas/liquid separator (9) into the sump of the gas scrubber (2), from where it is passed via conduit (12), circulating pump (13) and heat exchanger (15) back into the scrubber (2) as material stream (3). The heat exchanger (15) serves for the fine adjustment of the temperature of the washing liquid. Via conduit (7) fresh urea melt is fed into the scrubber (2), where it mixes with the urea-containing melt used as washing liquid. From the circuit of the urea-containing melt the material stream (14) is branched off and for use as raw material passed into the melamine synthesis (not shown).

Figure 2:
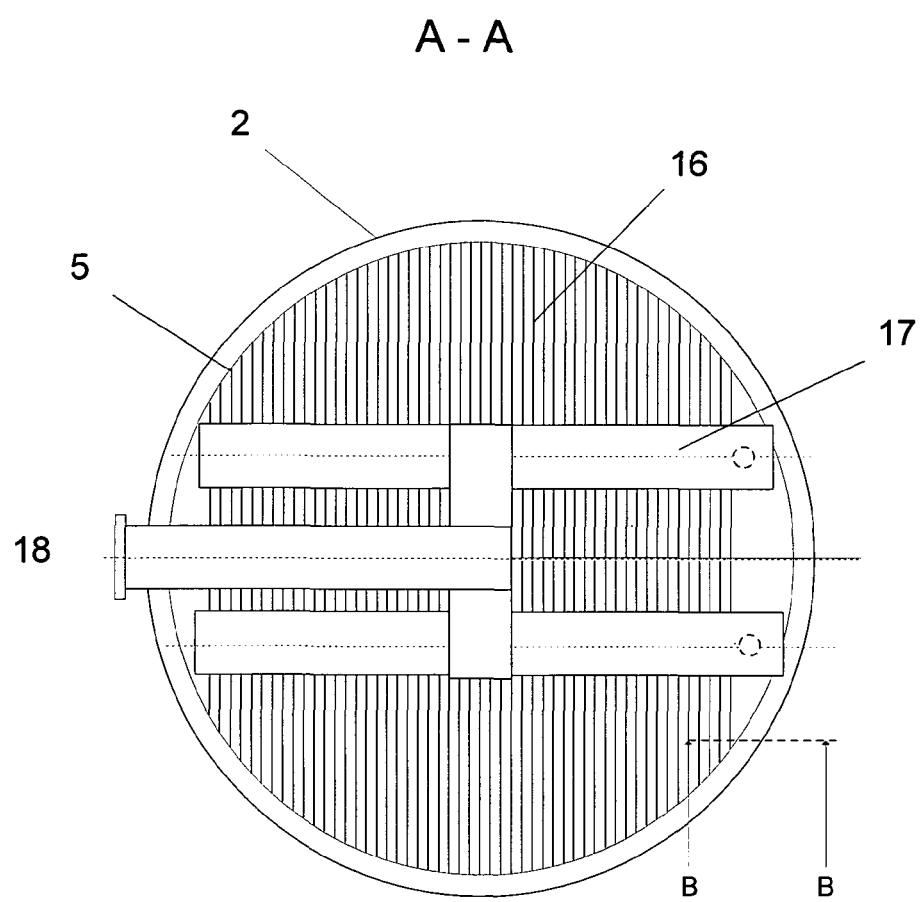
FIG. 2 is a cross-section of the gas scrubber of the present invention.

FIG. 2 shows the cross-section A-A. There is shown the heat exchanger (5) within the scrubber (2), comprising the thermoplates (16) arranged parallel to each other, the collecting conduits (17) and the connecting conduit (18) for the cooling medium.

Figure 3:
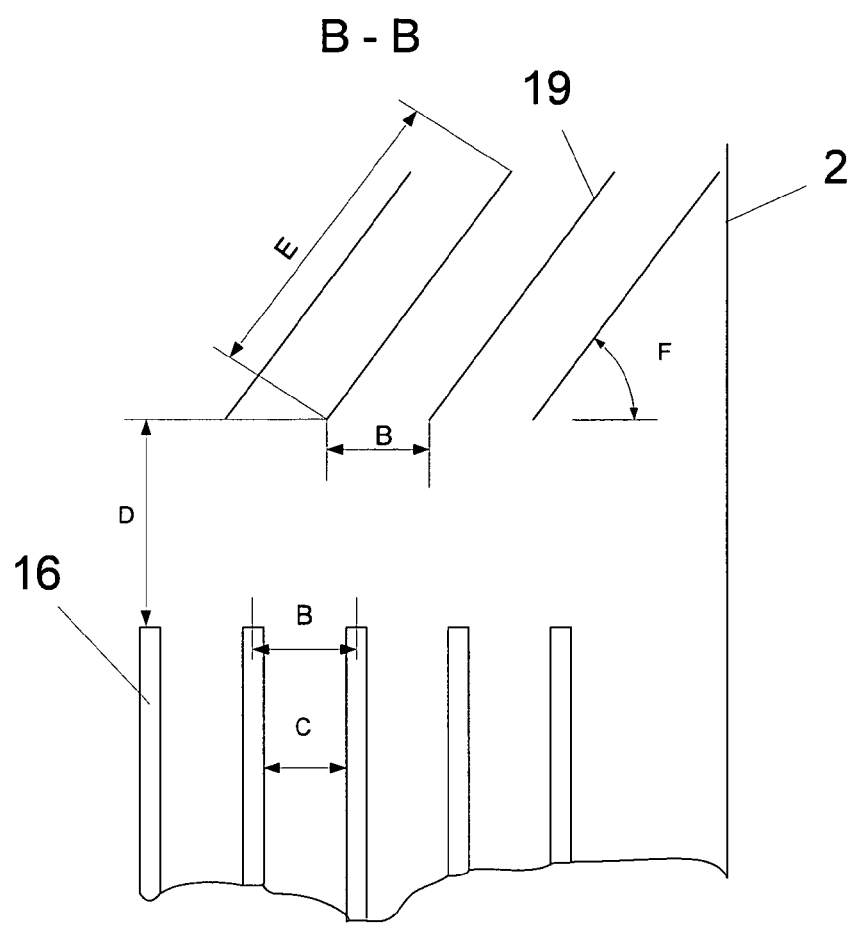
FIG. 3 is a longitudinal section of the wall of the gas scrubber.

FIG. 3 shows the longitudinal section B-B. There is shown a segment of the wall of the scrubber (2) and a segment of the heat exchanger (5) with its thermoplates (16). The same are arranged parallel to each other with a center distance B and a free intermediate distance C. In the distance D over the thermoplates (16), flow baffles (19) of the length E are installed. The horizontal distance between the flow baffles is as large as the center distance of the thermoplates.

Material Stream Table 1:

|  |  | Material stream no. | | | | | | | |
| --- | --- | --- | --- | --- | --- | --- | --- | --- | --- |
|  |  | 1 | 3 | 7 | 8 | 10 | 11 | 12 | 14 |
| Urea |  | residues | x | x | x | x |  | x | x |
| Process gas NH$_3$ + CO$_2$) |  | x |  |  | x |  | x |  |  |
| HNCO, residues |  | x |  |  |  |  |  |  |  |
| Melamine, residues |  | x | x |  | x | x |  | x | x |
| Flow rate | t/h | 150.0 | 854.0 | 10.0 | 1003.9 | 855.6 | 148.3 | 865.6 | 11.7 |
| Temp. | ° C. | 231 | 131 | 138 | 138 | 138 | 138 | 138 | 138 |
| Pressure | bar | 2.7 |  |  |  |  | 2.6 |  |  |
| State of matter | *) | g | li | li | g, li | li | g | li | li |

*) li = liquid
g = gaseous

The invention claimed is:

1. A gas scrubber comprising one or more heat exchangers integrated in a housing for cooling a gas/liquid mixture formed of the gas to be cleaned and a washing liquid, wherein the one or more heat exchangers contain one or more thermoplates, wherein the gas scrubber is the shape of a vertically arranged cylinder, and the heat exchanges each fill up the entire cross-section of the gas scrubber, wherein the thermoplates are arranged vertically upright in the heat exchangers and further wherein flow baffles are mounted over the thermoplates and arranged parallel to each other in such a way that a lower edge of the flow baffles extend parallel to an upper edge of the thermoplate at distance of between 5 to 15 cm, wherein the distance between the thermoplates is 7 to 45 mm and the gas/liquid mixture flows through gaps between the thermoplates and a cooling liquid flows within the thermoplates.

2. The gas scrubber according to claim 1 wherein the horizontal center distance (B) of the baffle plates is equal to the center distance of the thermoplates, wherein the depth E of the baffle plates is 10 to 30 cm, and wherein the baffle plates are arranged at an angle F of less than 90° relative to the vertical axis of the gas scrubber.

3. The gas scrubber according to claim 2 wherein the flow baffles are arranged in rows lying one beside the other and extending parallel to each other, with alternating angles F.

4. The gas scrubber according to claim 2 wherein the thermoplates of heat exchangers arranged downstream one behind the other are arranged at an angle of 90° relative to each other, rotated about the vertical axis of the gas scrubber.

5. A method for washing and cooling a gas by using a gas scrubber according to claim 1.

6. A method for washing and cooling a process waste gas of a melamine synthesis, said waste gas comprising ammonia and carbon dioxide as well as urea and isocyanic acid residues, by using a gas scrubber according to claim 1.

7. A method for washing and cooling a gas by using a gas scrubber according to claim 1, wherein the cooling liquid present within the thermoplates is evaporated by absorbing the heat from the gas/liquid mixture.

* * * * *